(12) United States Patent
Kim et al.

(10) Patent No.: US 10,596,224 B2
(45) Date of Patent: Mar. 24, 2020

(54) METHOD OF TREATING A WOUND, COMPRISING THE STEP OF ADMINISTERING A COMPOSITION INCLUDING A SUBSTANCE P

(71) Applicant: Biosolution Co., Ltd, Seoul (KR)

(72) Inventors: Da Jung Kim, Seoul (KR); Ji Hae Jang, Seoul (KR); Jung Sun Lee, Seoul (KR); Song Sun Jang, Seoul (KR)

(73) Assignee: Biosolutions Co., Ltd, Seoul (KR)

( * ) Notice: Subject to any disclaimer, the term of this patent is extended or adjusted under 35 U.S.C. 154(b) by 0 days.

(21) Appl. No.: 15/867,057

(22) Filed: Jan. 10, 2018

(65) Prior Publication Data

US 2018/0140658 A1 May 24, 2018

Related U.S. Application Data

(63) Continuation-in-part of application No. PCT/KR2016/004539, filed on Apr. 29, 2016.

(51) Int. Cl.

| | |
|---|---|
| *A61K 38/08* | (2019.01) |
| *A61K 47/02* | (2006.01) |
| *A61K 47/26* | (2006.01) |
| *A61K 47/38* | (2006.01) |
| *A61K 9/08* | (2006.01) |
| *C07K 7/22* | (2006.01) |
| *C07K 7/06* | (2006.01) |
| *A61K 38/04* | (2006.01) |
| *A61L 26/00* | (2006.01) |

(52) U.S. Cl.
CPC ............... *A61K 38/08* (2013.01); *A61K 9/08* (2013.01); *A61K 38/046* (2013.01); *A61K 47/02* (2013.01); *A61K 47/26* (2013.01); *A61K 47/38* (2013.01); *A61L 26/0066* (2013.01); *A61L 2300/214* (2013.01); *A61L 2300/802* (2013.01)

(58) Field of Classification Search
CPC ...... A61K 38/046; A61K 38/08; A61K 47/02; A61K 47/26; A61K 47/38; A61K 9/08; C07K 7/22; C07K 7/06
USPC .......................... 514/5.2, 9.4, 21.6; 530/327
See application file for complete search history.

(56) References Cited

U.S. PATENT DOCUMENTS

| | | | | |
|---|---|---|---|---|
| 7,348,360 B2 * | 3/2008 | Hensley | ............... | A61K 9/0043 424/641 |
| 7,425,528 B2 * | 9/2008 | Simonsen | ............... | A21D 8/042 424/408 |
| 8,129,408 B2 * | 3/2012 | Ortyl | .................... | A61K 9/2054 514/317 |
| 8,222,210 B2 | 7/2012 | Reid et al. | | |
| 2005/0250175 A1 * | 11/2005 | Nomura | ............... | A61K 9/0014 435/34 |
| 2006/0165750 A1 * | 7/2006 | Reatti | .................. | A01N 25/006 424/410 |
| 2007/0154448 A1 * | 7/2007 | Reid | .................... | A61K 38/046 424/85.1 |

FOREIGN PATENT DOCUMENTS

| | | |
|---|---|---|
| JP | 2008-518020 A | 5/2008 |
| JP | 2002-226395 A | 8/2014 |
| KR | 10-0593397 B1 | 6/2006 |
| KR | 10-2014-0102026 A | 8/2014 |

OTHER PUBLICATIONS

D. Dobie and J. Gray, "Fusidic acid resistance in *Staphylococcus aureus*", Arch Dis Child, (2004), 89:74-77.
M. Nakamura, et al. "Restoration of Corneal Epithelial Barrier Function and Wound Healing by Substance P and IGF-1 in Rats with Capsaicin-Induced Neurotrophic Keratopathy", Invest Ophthalmol Vis Sci, (Jul. 2003), 44(7):2937-2940.
International Search Report dated Dec. 28, 2016 in connection with PCT International Application No. PCT/KR2016/004539.

\* cited by examiner

*Primary Examiner* — Julie Ha
(74) *Attorney, Agent, or Firm* — John P. White; Cooper & Dunham LLP

(57) ABSTRACT

Provided are a pharmaceutical composition for wound healing including a surfactant, an antioxidant, a thickener, and SP, a method of treating a wound including administering the pharmaceutical composition to a subject, and a quasi-drug composition for wound healing including a surfactant, an antioxidant, a thickener, and substance.
The pharmaceutical composition of the present invention reduces a wound size, generates new blood vessels, shows dermal and epidermal regeneration effects, matures granulation tissues, and synthesizes collagen, and thus may be used for wound healing.

8 Claims, 14 Drawing Sheets

Specification includes a Sequence Listing.

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: substance P

<400> SEQUENCE: 1

Arg Pro Lys Pro Gln Gln Phe Phe Gly Leu Met
1               5                   10

METHOD OF TREATING A WOUND, COMPRISING THE STEP OF ADMINISTERING A COMPOSITION INCLUDING A SUBSTANCE P

CROSS-REFERENCE TO RELATED APPLICATIONS

This application is a continuation-in-part of PCT International Application No. PCT/KR2016/004539, filed Apr. 29, 2016, claiming priority of Korean Patent Application No. KR 10-2016-0042913, filed Apr. 7, 2016.

REFERENCE TO A SEQUENCE LISTING

This application incorporates by reference nucleotide and/or amino acid sequences which are present in the file named "180110_90229_Sequence_Listing_CAE.txt", which is 424 bytes in size, and which was created Jan. 10, 2018 in the IBM-PC machine format, having an operating system compatibility with MS-Windows, which is contained in the text file filed Jan. 10, 2018 as part of this application.

TECHNICAL FIELD

The present invention relates to a method of treating a wound including administering a pharmaceutical composition for wound healing including a thickener, an antioxidant, a surfactant, and substance P (SP), pharmaceutical composition for wound healing including a thickener, an antioxidant, a surfactant, and SP, and a quasi-drug composition for wound healing including a thickener, an antioxidant, a surfactant, and SP.

BACKGROUND ART

Wound healing is a complex process whereby a skin, another organ or tissue repairs itself after an injury. On the normal skin, the epidermis (outermost layer) and the dermis (inner or deep layer) form a protective barrier against the external environment. Once the protective barrier is broken, a normal physiological process of wound healing is immediately set in motion. However, health or an age of the injured, a disease such as diabetes, or the presence of a foreign material or necrotic tissue may influence a wound healing rate. If the wound healing is delayed, there is a risk of secondary infection through the wound site. Further, incomplete control of wound resolution in some wounds causes excessive scar formation, resulting in a problem of functionally and cosmetically inferior scar formation. Thus, when a wound occurs, it is important to heal the wound quickly without side effects.

At present, DongWha Pharmaceutical's Fucidin, Dongkook Pharmaceutical's Madecassol, etc. are representative commercially-available products used for wound healing. However, there is a report that *Staphylococcus* aureus resistant to fusidic acid which is a main ingredient of Fucidin is increasing (*Arch Dis Child* 2004; 89:74-44). It has also been continuously reported that use of Fucidin or Madecassol causes side effects such as allergic reactions, rash, etc. Accordingly, there is a growing need for researches on new drugs.

Meanwhile, a neuropeptide consisting of 11 amino acids, SP is reported to be expressed in some cells and granulation tissues. Some studies have reported that SP improves corneal epithelial barrier function in the corneal epithelial wound and exhibits therapeutic effect on keratopathy (*Invest Ophthalmol Vis Sci*. 2003 July; 44(7): 2937-40). Further, Korean Patent Publication No. 10-2006-0037176 discloses that SP and mesenchymal stem cells may be used to develop a therapeutic agent effective for wound healing. However, there is a disadvantage that the stem cells easily die when they are practically used as a raw material for cosmetics, and cause cytotoxicity after death. Therefore, there is still a demand for the development of a wound healing agent using SP.

Accordingly, the present inventors have made extensive efforts to improve the wound healing efficacy of drugs including SP, and as a result, they found that a pharmaceutical composition including an antioxidant, a surfactant, a thickener, and SP shows excellent wound healing efficacy compared to commercially available products, thereby completing the present invention.

DISCLOSURE

Technical Problem

An object of the present invention is to provide a method of treating a wound, including administering a composition including a thickener, an antioxidant, a surfactant, and SP to a subject in need thereof.

Another object of the present invention is to provide a pharmaceutical composition for wound healing including a thickener, an antioxidant, a surfactant, and SP.

Still another object of the present invention is to provide a quasi-drug composition for wound healing including a thickener, an antioxidant, a surfactant, and SP.

Technical Solution

The present inventors have made extensive efforts to improve the wound healing efficacy of drugs including SP, and as a result, they found that a composition including an antioxidant, a surfactant, a thickener, and SP shows excellent wound healing efficacy, compared to commercially available products, thereby completing the present invention.

Advantageous Effects

The composition according to the present invention has excellent effects of reducing a wound size, generating blood vessels, and regenerating dermis and epidermis, and thus may be used as a drug having improved wound healing efficacy.

BRIEF DESCRIPTIONS OF THE DRAWINGS

Figure 3A:
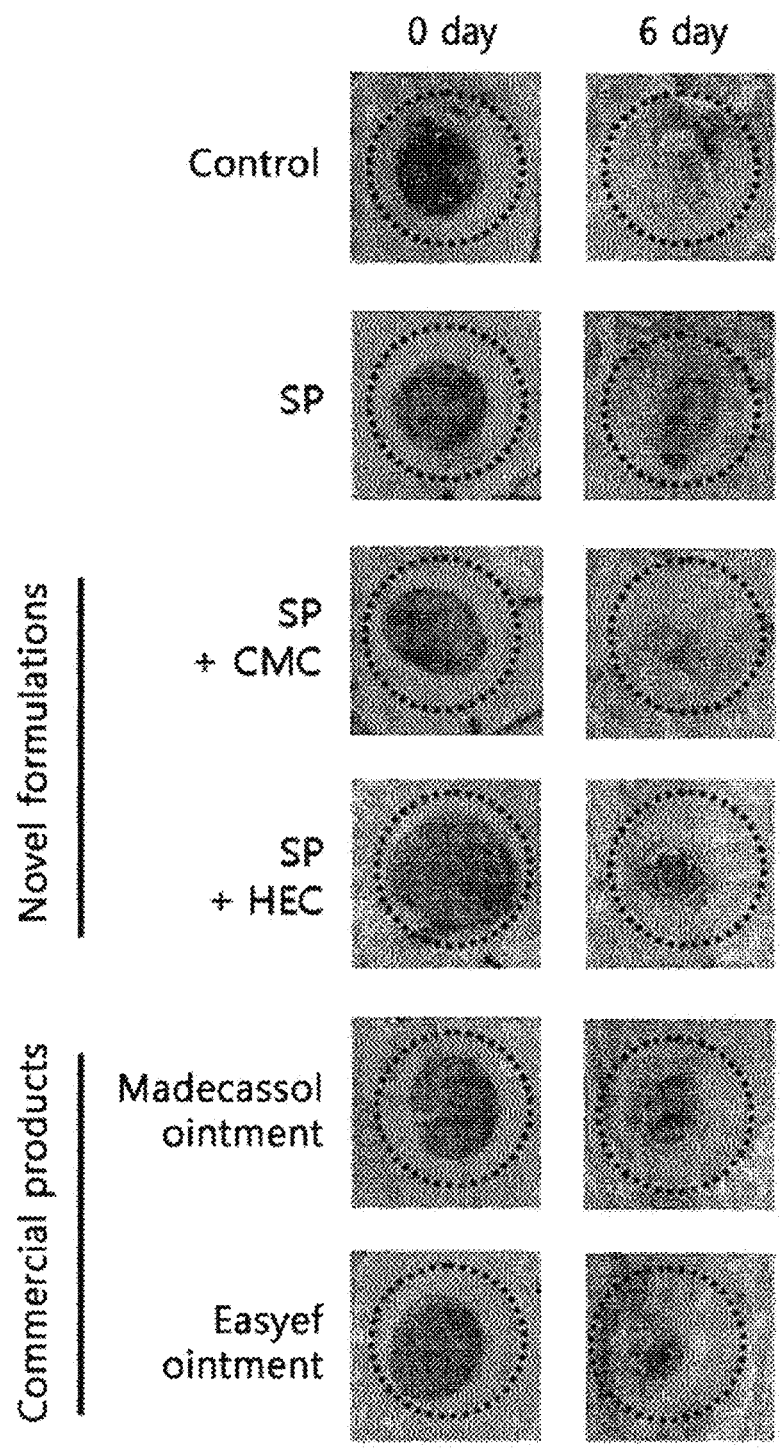
Figure 3B:
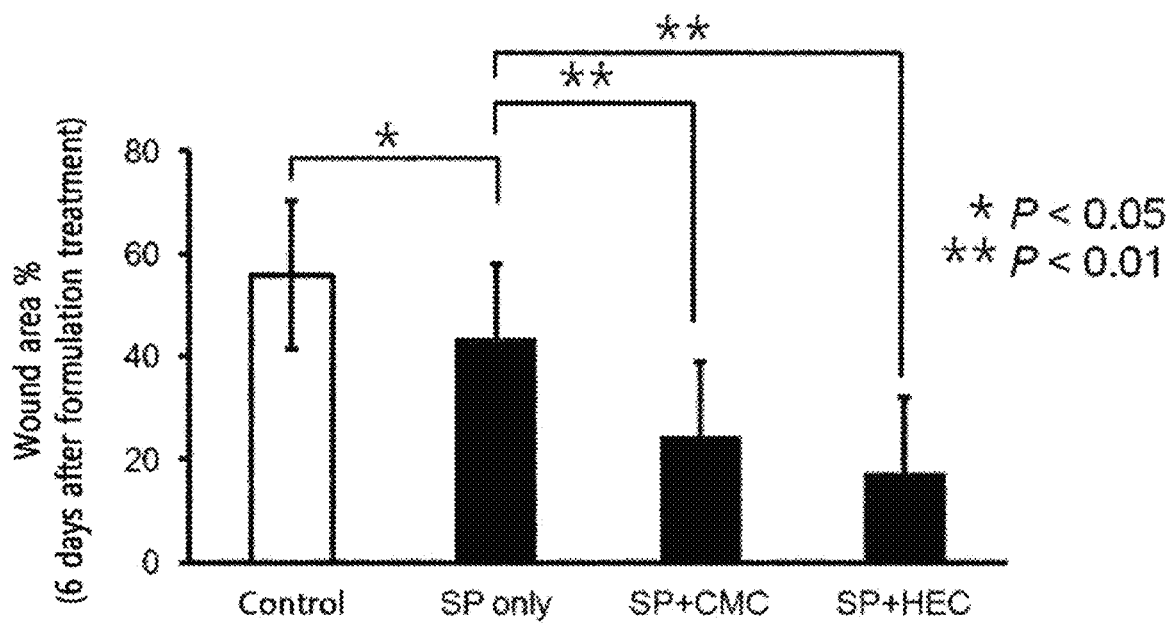
Figure 3C:
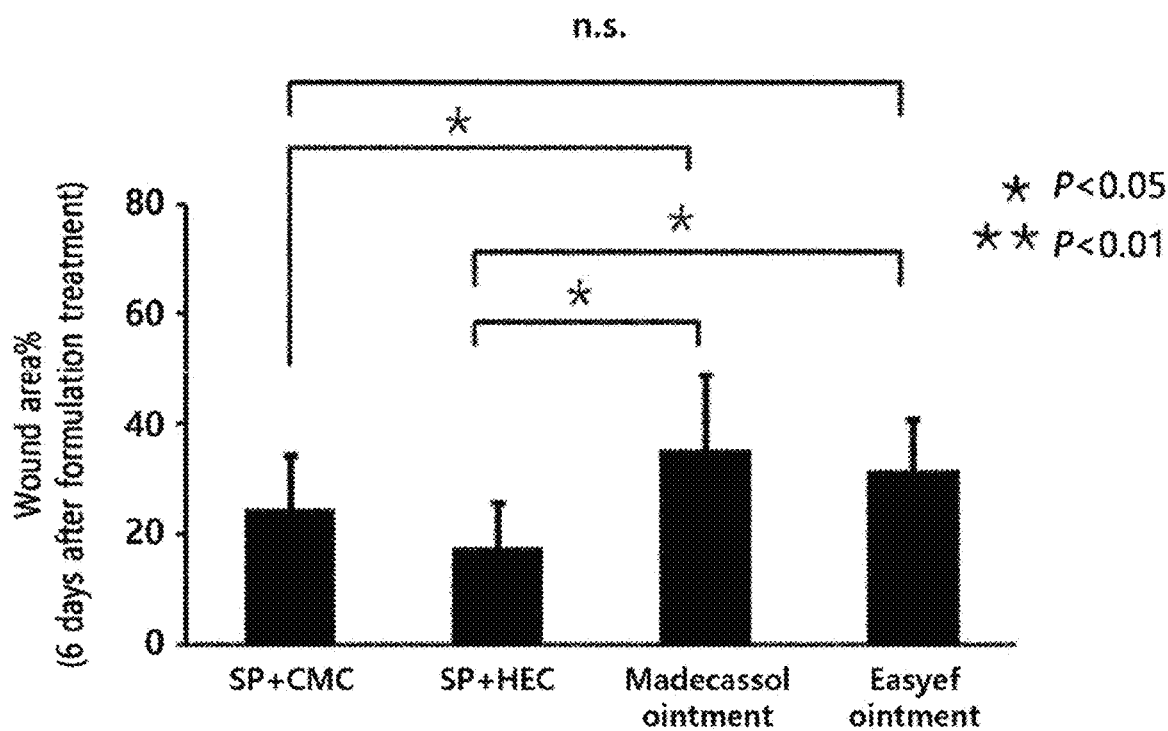
Figure 4A:
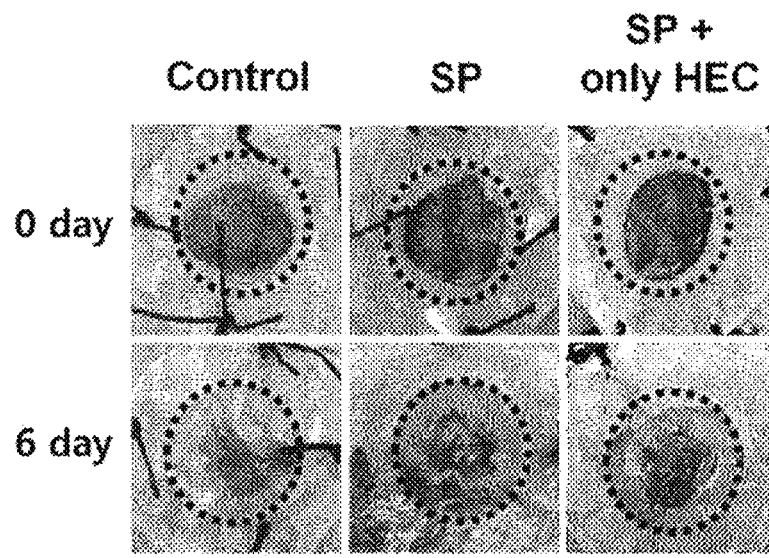
Figure 4B:
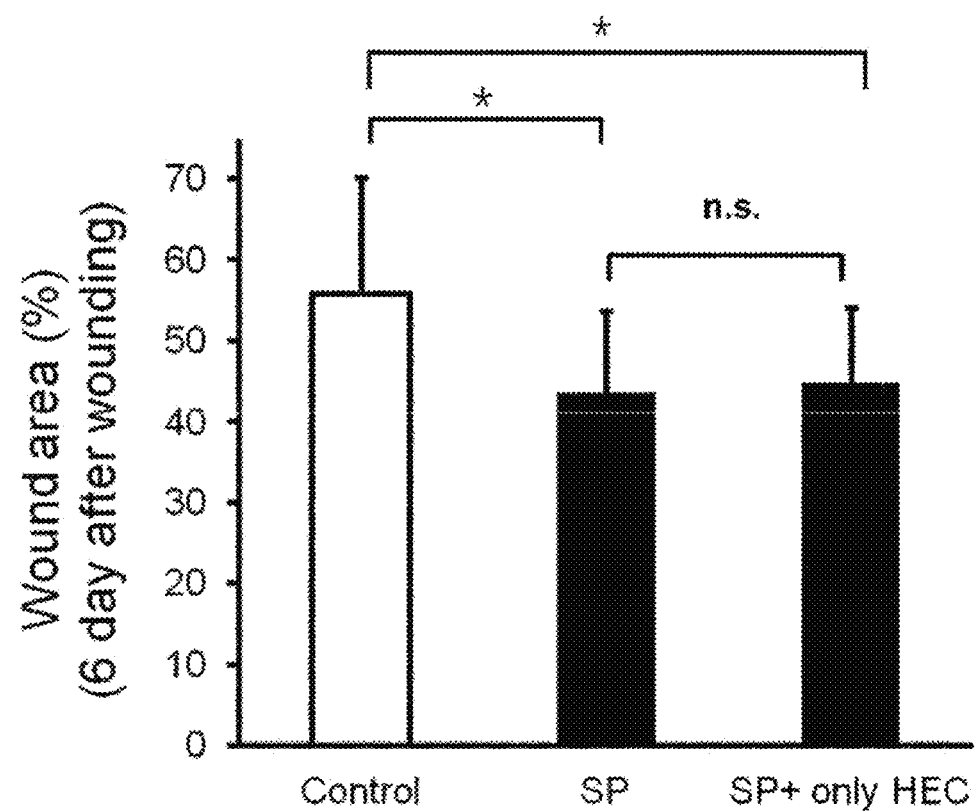
Figure 5:
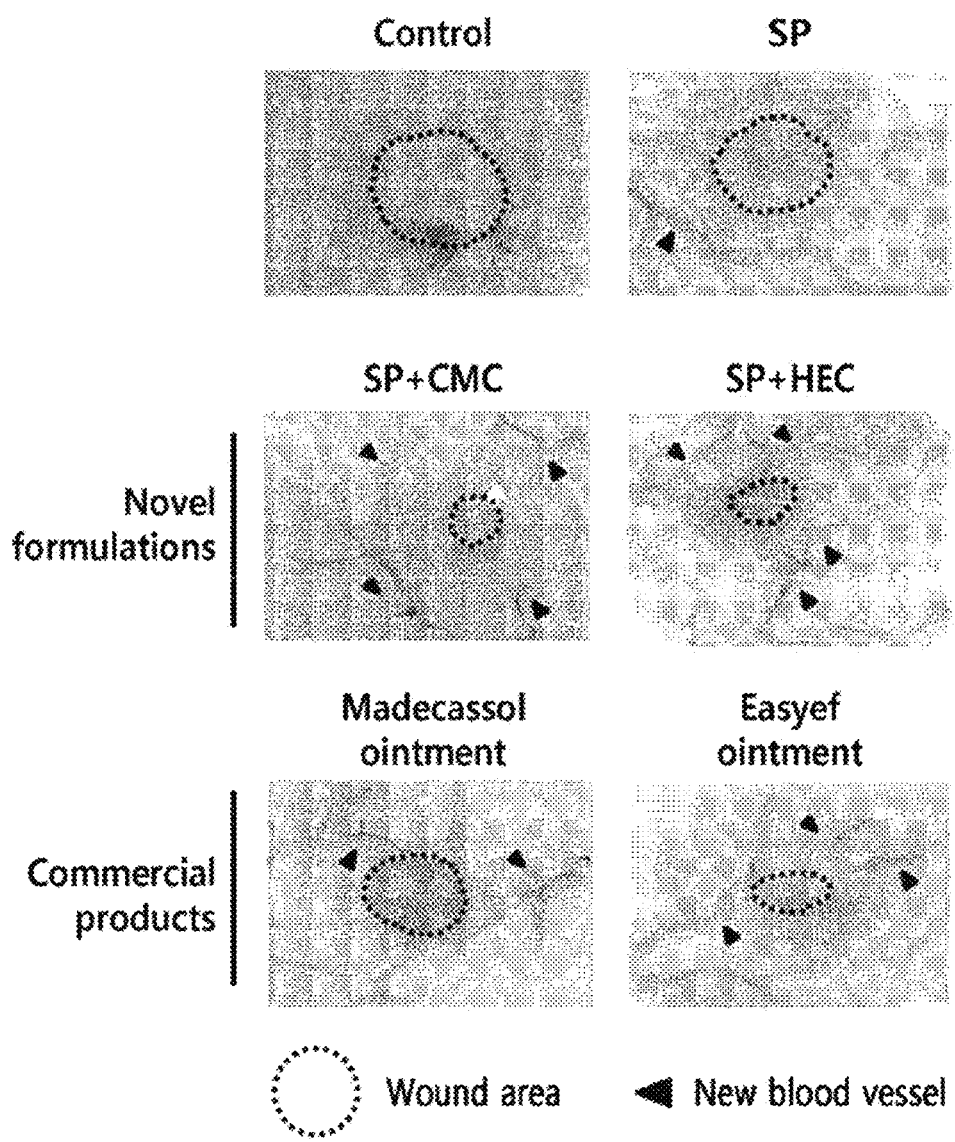
Figure 6A:
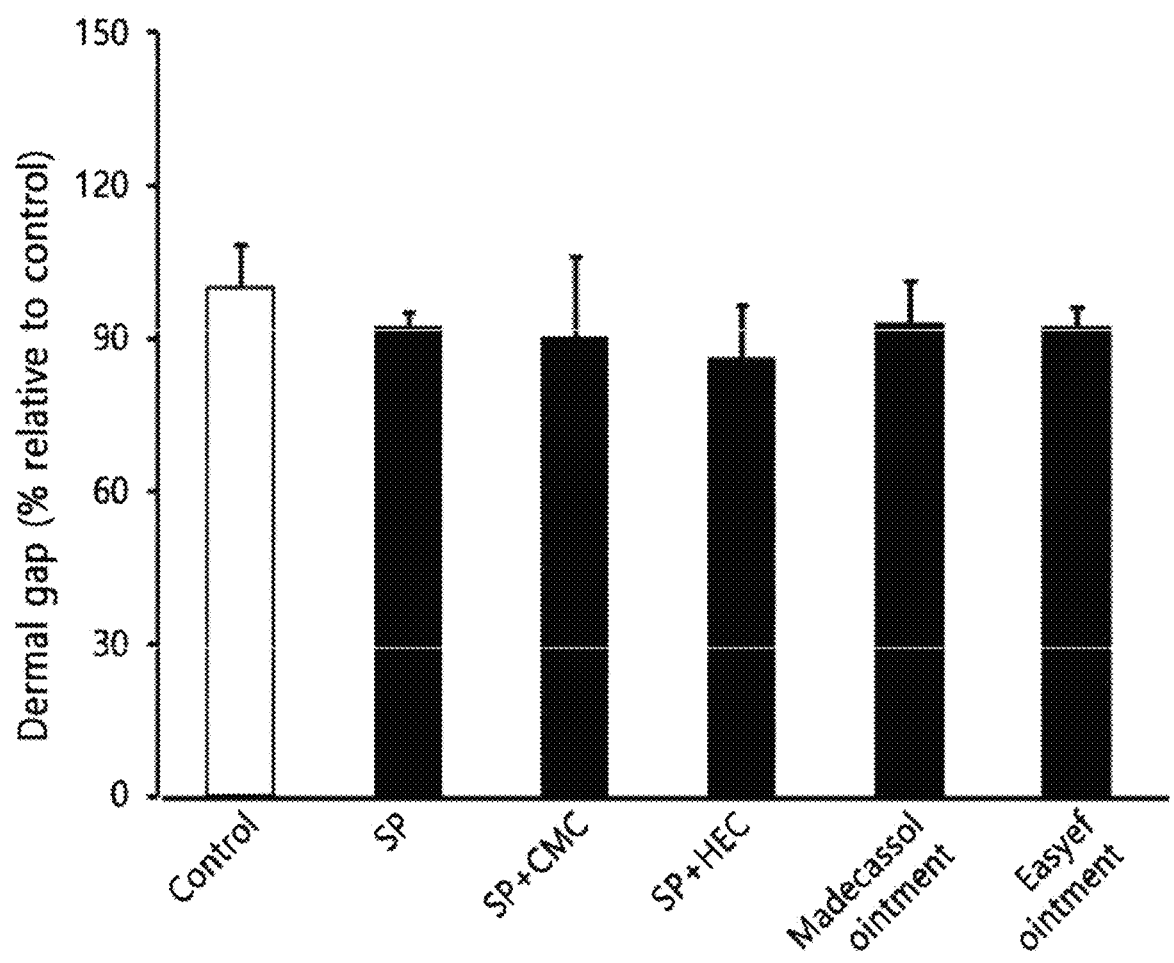
Figure 6B:
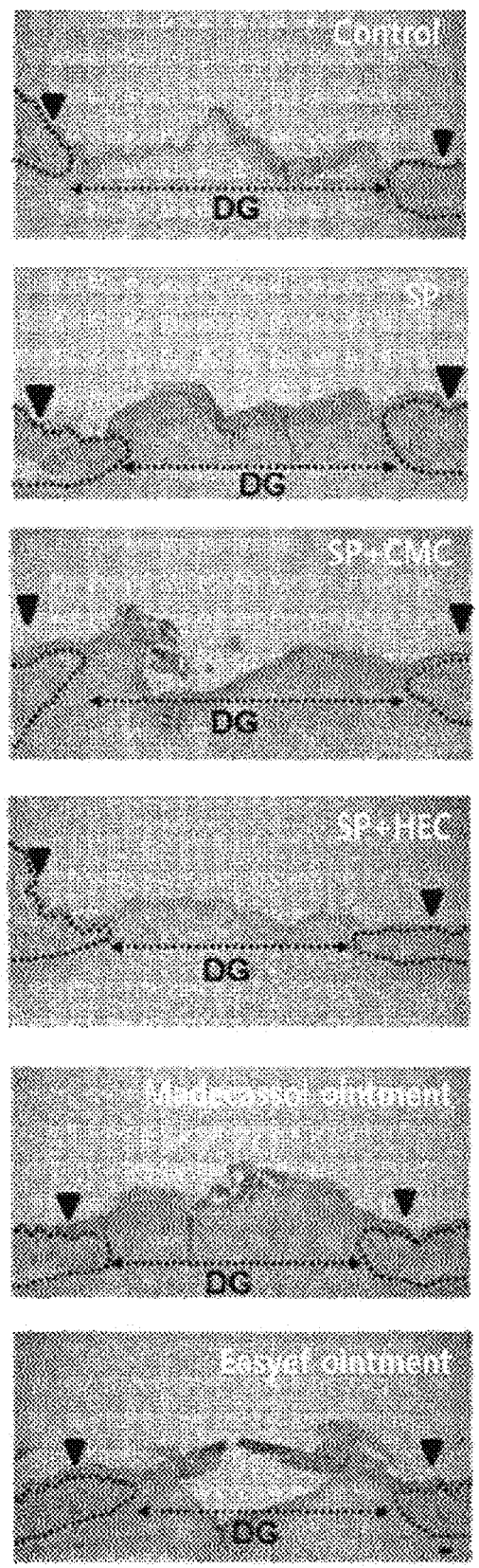
Figure 7A:
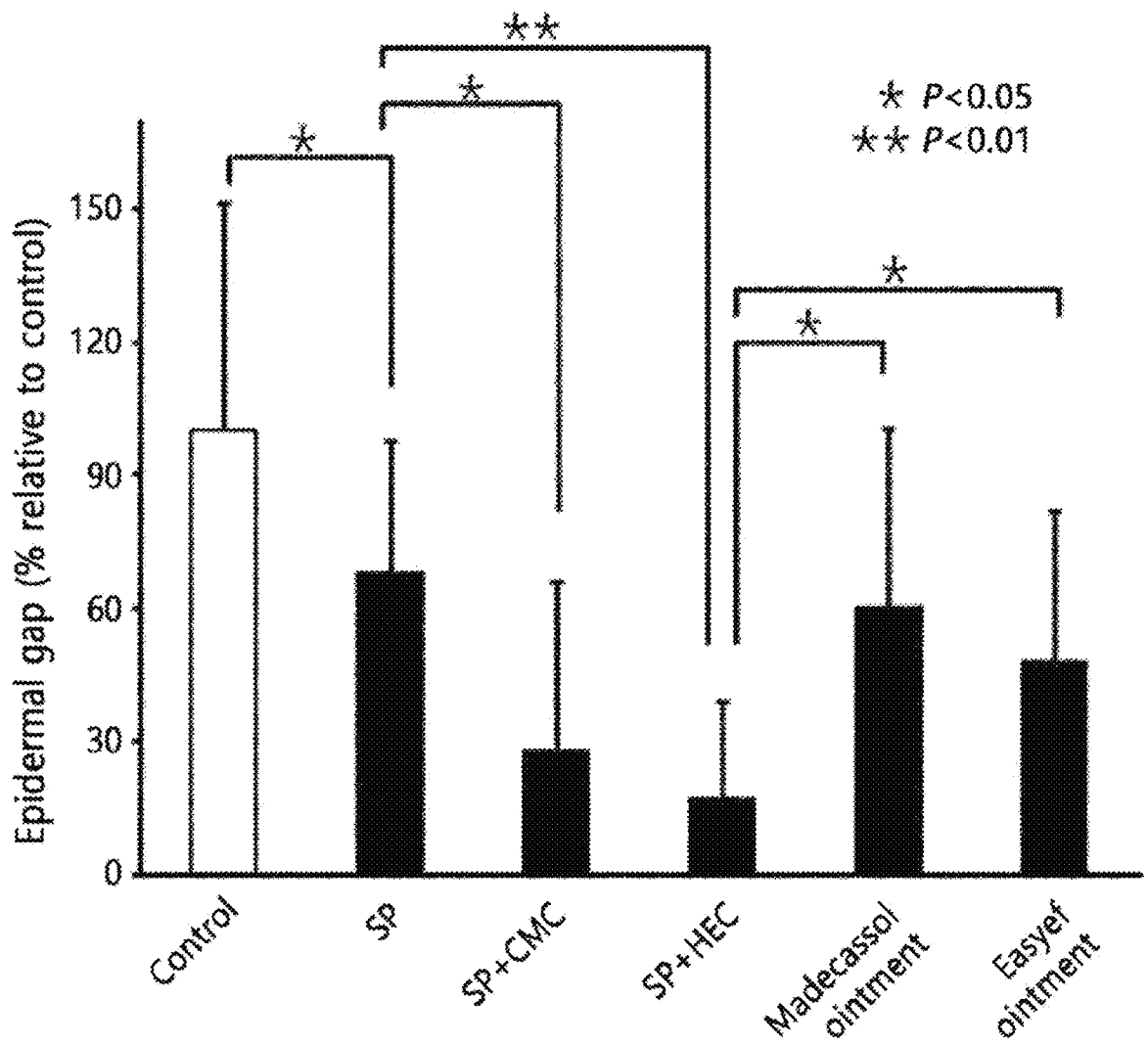
Figure 7B:
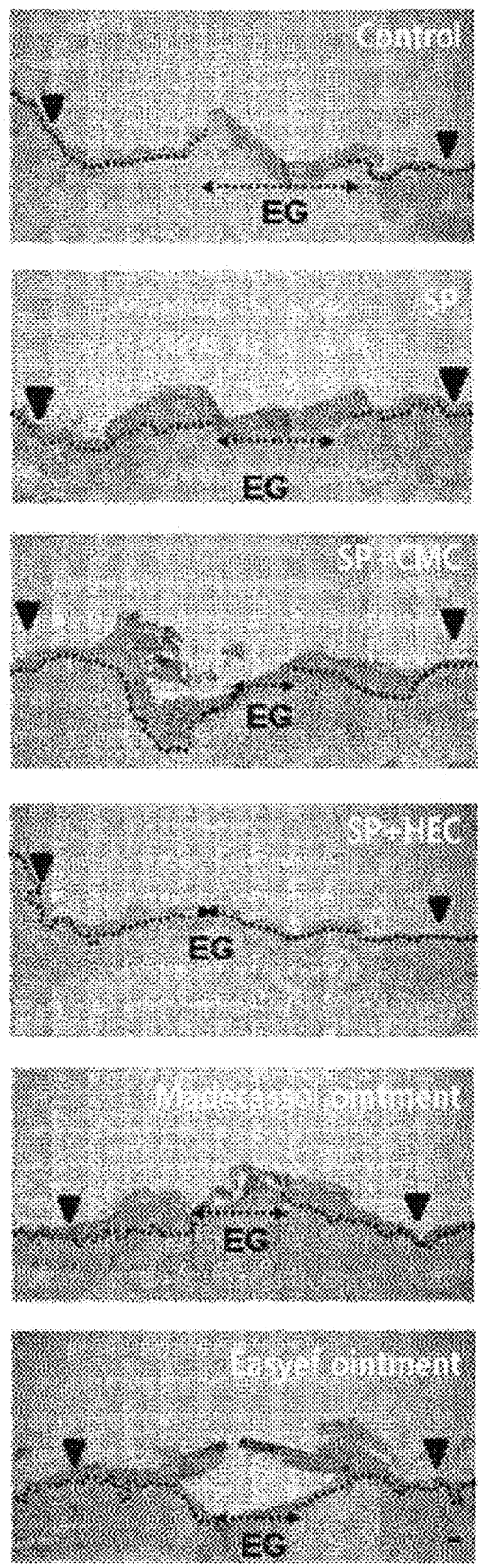
Figure 8:
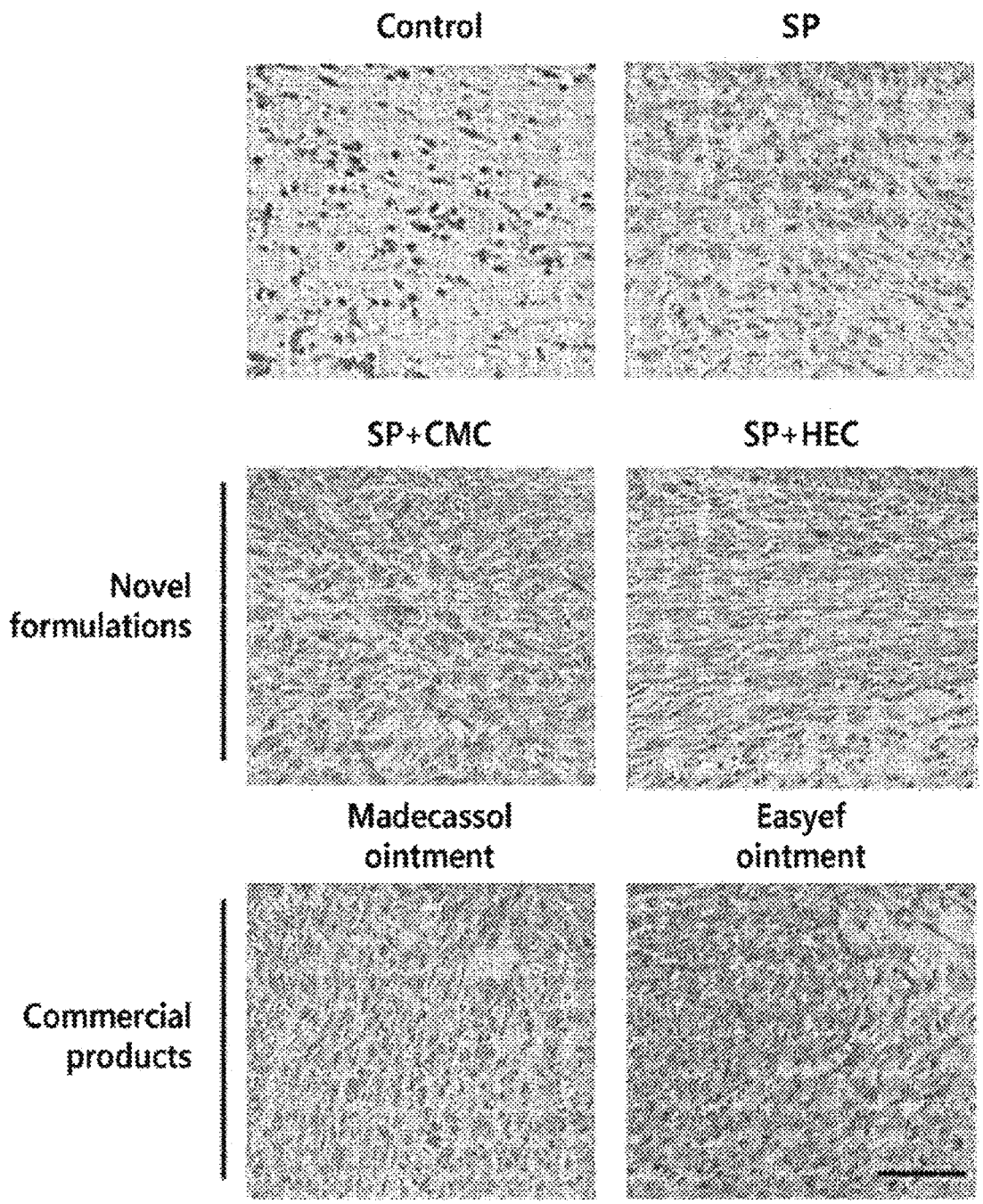
Figure 9:
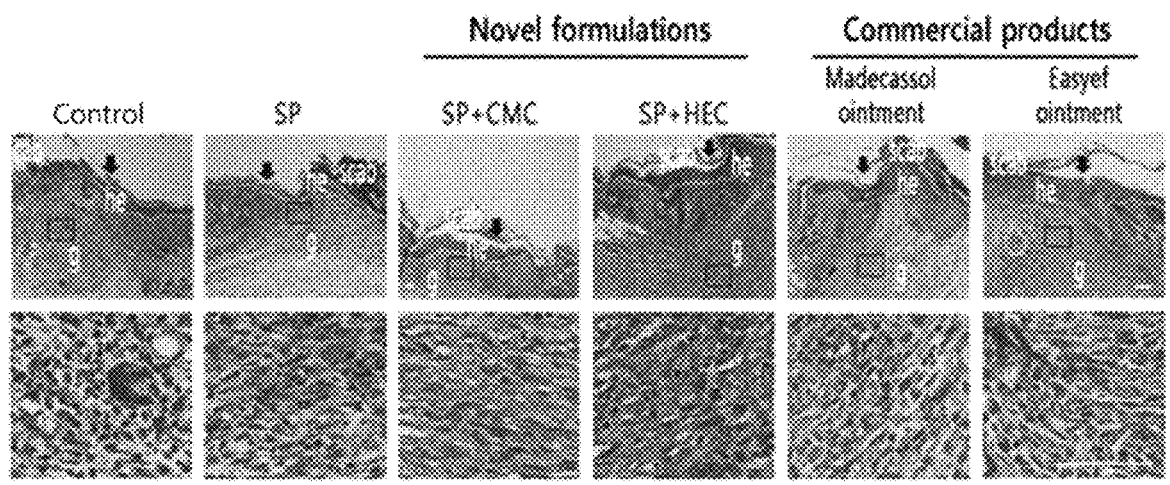
Figure 10A:
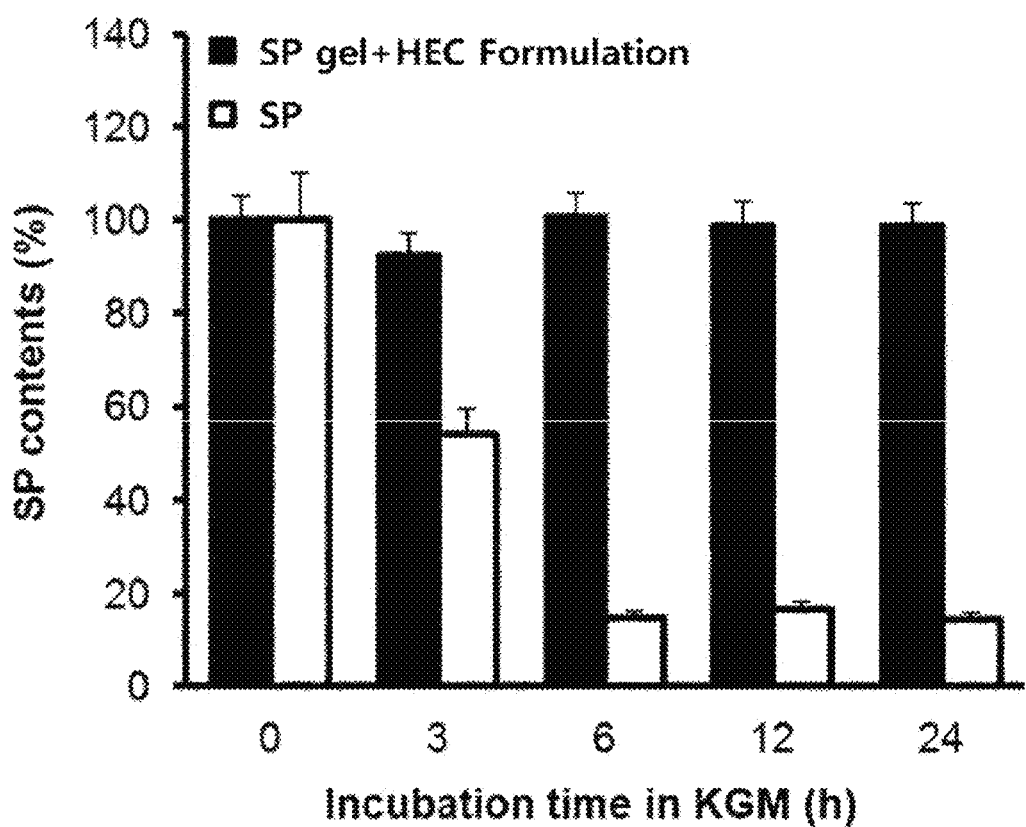
Figure 10B:
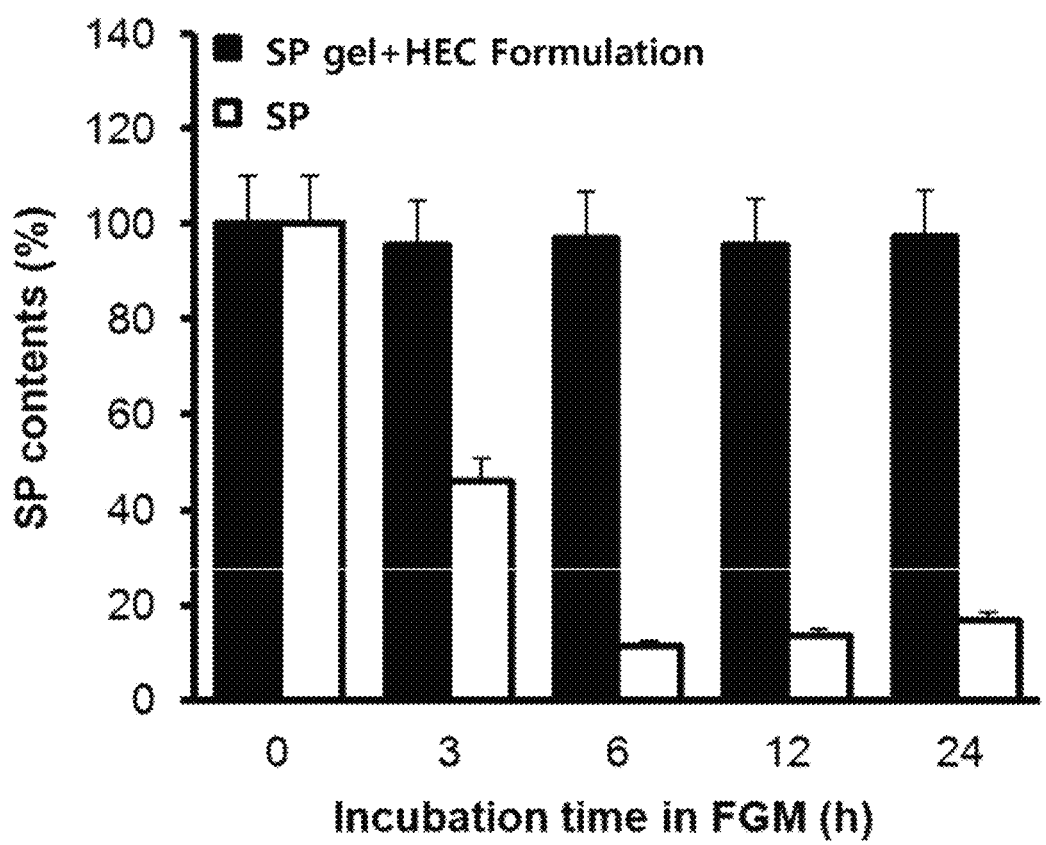
Figure 10C:
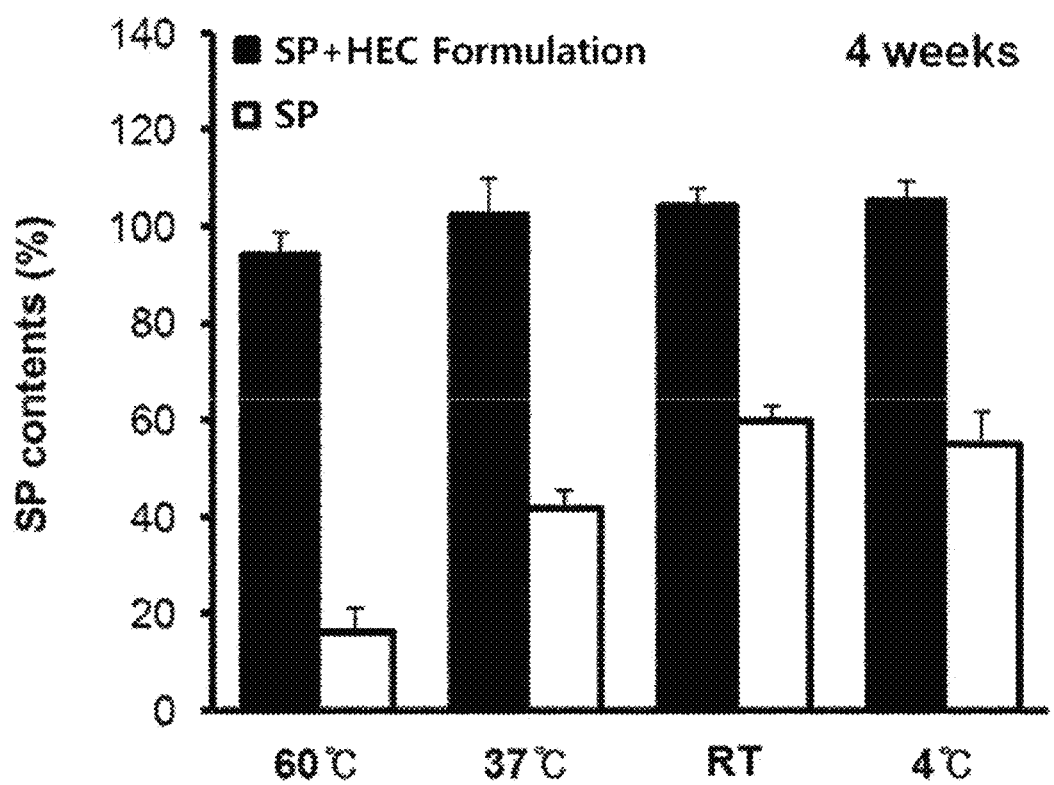

FIG. 3A is an image showing the wound size at 0 day and 6 days after treatment of skin wound mouse models with SP, SP+ carboxymethyl cellulose (CMC)+polysorbate 80+sodium thiosulfate formulation, SP+ hydroxyethyl cellulose (HEC)+polysorbate 80+sodium thiosulfate formulation, Madecassol ointment, and Easyef ointment;

FIG. 3B is a graph showing quantification of the reduced wound size 6 days after treatment of skin wound mouse models with SP, SP+CMC+polysorbate 80+sodium thiosulfate, and SP+HEC+polysorbate 80+sodium thiosulfate;

FIG. 3C is a graph showing quantification of the reduced wound size 6 days after treatment of skin wound mouse models with SP+CMC+polysorbate 80+sodium thiosulfate, SP+HEC+polysorbate 80+sodium thiosulfate, Madecassol ointment, and Easyef ointment;

FIG. 4A is an image showing the wound size at 0 day and 6 days after treatment of skin wound mouse models with SP and SP+Only HEC;

FIG. 4B is a graph showing quantification of the reduced wound size 6 days after treatment of skin wound mouse models with SP and SP+Only HEC;

FIG. 5 is an image showing angiogenesis 6 days after treatment of the wound skin of skin wound mouse models with SP, SP+CMC+polysorbate 80+sodium thiosulfate, SP+HEC+polysorbate 80+sodium thiosulfate, Madecassol ointment and Easyef ointment;

FIG. 6A is a graph showing quantification of dermal regeneration 6 days after treatment of the wound skin of skin wound mouse models with SP, SP+CMC+polysorbate 80+sodium thiosulfate, SP+HEC+polysorbate 80+sodium thiosulfate, Madecassol ointment and Easyef ointment;

FIG. 6B is an image showing dermal regeneration 6 days after treatment of the wound skin of skin wound mouse models with SP, SP+CMC+polysorbate 80+sodium thiosulfate, SP+HEC+polysorbate 80+sodium thiosulfate, Madecassol ointment and Easyef ointment;

FIG. 7A is a graph showing quantification of epidermal regeneration 6 days after treatment of the wound skin of skin wound mouse models with SP, SP+CMC+polysorbate 80+sodium thiosulfate, SP+HEC+polysorbate 80+sodium thiosulfate, Madecassol ointment and Easyef ointment;

FIG. 7B is an image showing epidermal regeneration 6 days after treatment of the wound skin of skin wound mouse models with SP, SP+CMC+polysorbate 80+sodium thiosulfate, SP+HEC+polysorbate 80+sodium thiosulfate, Madecassol ointment and Easyef ointment;

FIG. 8 is an image showing granulation tissue maturation 6 days after treatment of the wound skin of skin wound mouse models with SP, SP+CMC+polysorbate 80+sodium thiosulfate, SP+HEC+polysorbate 80+sodium thiosulfate, Madecassol ointment and Easyef ointment;

FIG. 9 is an image showing collagen synthesis 6 days after treatment of the wound skin of skin wound mouse models with SP, SP+CMC+polysorbate 80+sodium thiosulfate, SP+HEC+polysorbate 80+sodium thiosulfate, Madecassol ointment and Easyef ointment;

FIG. 10A is a graph showing changes in SP contents over time after treatment of skin wound mouse models with SP and SP+HEC+polysorbate 80+sodium thiosulfate and incubation in KGM;

FIG. 10B is a graph showing changes in SP contents over time after treatment of skin wound mouse models with SP and SP+HEC+polysorbate 80+sodium thiosulfate and incubation in FGM; and FIG. 10C is a graph showing changes in SP contents according to temperature conditions after treatment of skin wound mouse models with SP and SP+HEC+polysorbate 80+sodium thiosulfate.

BEST MODE

An aspect of the present invention provides a method of treating a wound, including administering a composition including a thickener, an antioxidant, a surfactant, and SP consisting of an amino acid sequence of SEQ ID NO: 1 to a subject in need thereof.

The composition including the thickener, the antioxidant, the surfactant, and SP may be a pharmaceutical composition for wound healing.

Specifically, a substance stabilizing a drug varies depending on the kind of the drug, and the present invention is characterized by developing an optimum composition capable of improving the wound healing effect of SP.

The present inventors confirmed that the composition including the thickener, the antioxidant, the surfactant, and SP shows excellent angiogenic effect and epidermal regeneration effect, forms mature granulation tissues well, and improves collagen synthesis, compared to SP itself or commercially available wound healing agents, thereby completing the present invention.

In the composition of the present invention, the SP refers to a neuropeptide consisting of "Arg-Pro-Lys-Pro-Gln-Gln-Phe-Phe-Gly-Leu-Met-NH2" amino acids of SEQ ID NO: 1. It is known that the SP is widely distributed in the central nerve system such as brain and spinal cord and peripheral organs and functions to transmit pain sensation in the primary sensory neuron.

A concentration of SP included in the composition of the present invention may be 0.1 μg/ml to 100 μg/ml, and specifically 3 μg/ml to 8 μg/ml.

Figure 1:
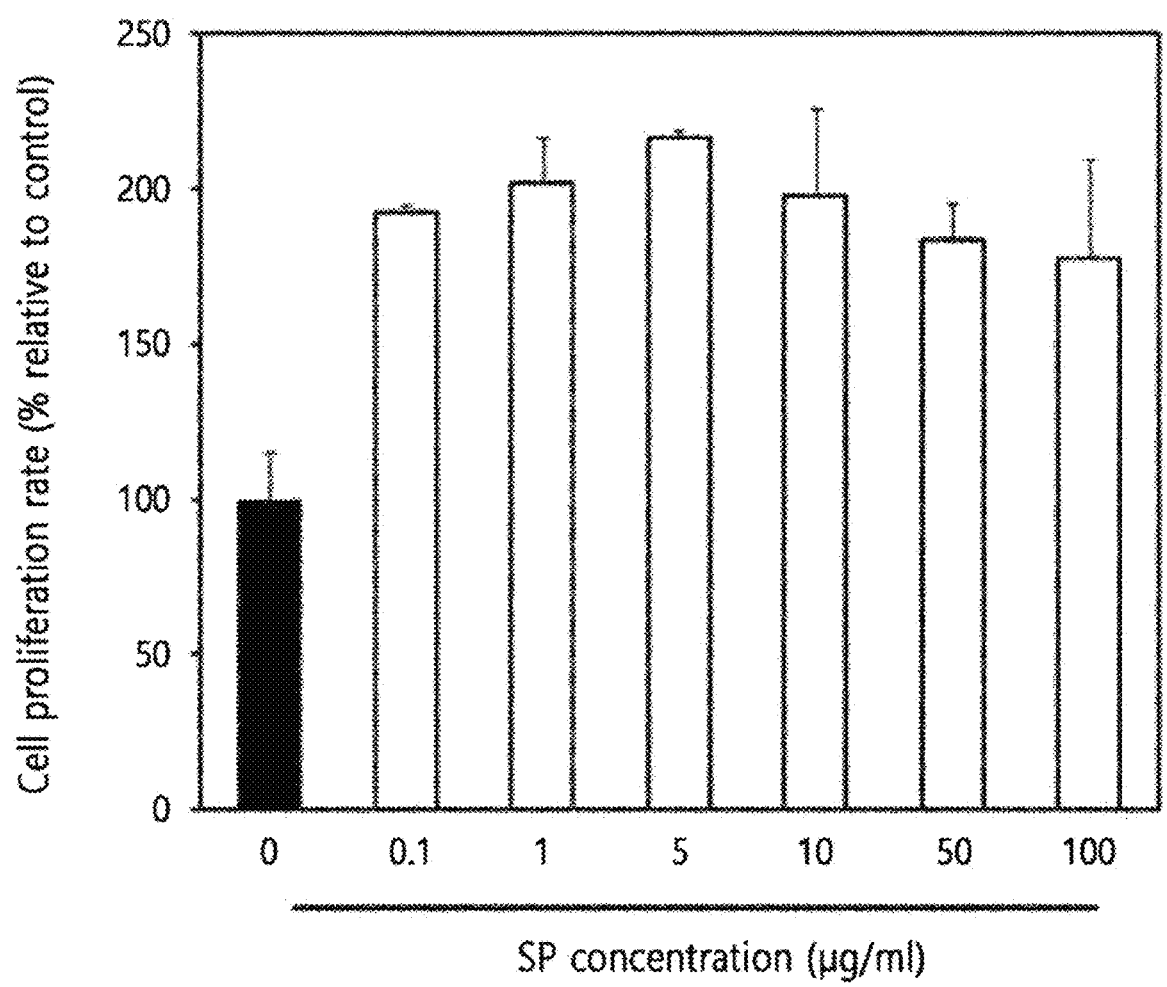
FIG. 1 is a graph showing a cell proliferation rate according to a concentration of SP treated to human dermal fibroblasts.

In an Example of the present invention, it was demonstrated that SP of 0.1 μg/ml to 100 μg/ml shows an excellent cell proliferative effect, compared to a negative control group, and in particular, SP of 3 μg/ml to 8 μg/ml shows the most excellent cell proliferative effect (FIG. 1).

Therefore, it can be seen that when the concentration of SP is 0.1 μg/ml to 100 μg/ml, it shows an excellent cell proliferative effect, and enables the drug of the present invention to exhibit an excellent wound healing effect.

In the composition of the present invention, the thickener refers to an additive that is added to provide viscosity, and is also called a thickening agent or thickening stabilizer.

Conventional thickener which may be used in the art may be used as the thickener without limitation, and specifically, any compound commercially available may be purchased or may be prepared by a conventional method known in the art, and any extract obtained from natural products or components contained therein may be used, but the thickener is not limited thereto, and any component which has the role of an thickener may be freely selected and used regardless of its route of entry. Specifically, sodium carboxymethylcellulose or hydroxyethyl cellulose may be used, but it is not limited thereto. More specifically, in the present invention, the thickener may be hydroxyethyl cellulose.

A content of the thickener may be 1% by weight to 20% by weight with respect to the total weight of the composition of the present invention. If the content of the thickener is 1% by weight or less with respect to the total weight of the composition, there is a problem in the stability of the pharmaceutical composition. If the content of the thickener is 20% by weight or more with respect to the total weight of the composition, viscosity of the pharmaceutical composition is excessively increased and thus the composition becomes unsuitable for application.

In an Example of the present invention, it was demonstrated that the composition including sodium carboxymethylcellulose or hydroxyethyl cellulose as the thickener has an excellent wound size-reducing effect, compared to SP and commercially available wound healing agents (FIGS. 3A and 3B). In particular, the composition including hydroxyethyl cellulose as the thickener has an excellent wound size-reducing effect, compared to compositions including different kinds of thickeners (FIG. 3C).

Therefore, the wound healing effect may vary depending on the kind of the thickener included in the composition of the present invention, and when sodium carboxymethylcellulose or hydroxyethyl cellulose is included as the thickener, the excellent wound healing effect may be obtained. In particular, when the thickener is hydroxyethyl cellulose, it may be suitable for the pharmaceutical composition for wound healing.

The composition of the present invention may be used as a single formulation, or may be prepared as a complex formulation by further including a known drug which is approved to have the wound healing effect. By formulating using a pharmaceutically acceptable carrier or excipient, the composition may be prepared as a unit dosage form or contained in a multidose container.

The "pharmaceutically acceptable carrier" refers to a carrier, excipient, or diluent that does not cause significant irritation to an organism and does not abrogate biological activities and properties of an administered compound, and specifically, may be a non-naturally occurring carrier. The kind of the carrier usable in the present invention is not particularly limited, and any pharmaceutically acceptable carrier may be used as long as it is commonly used in the art. Non-limiting examples of the carrier may include saline, sterile water, Ringer's solution, buffered physiological saline, an albumin infusion solution, a dextrose solution, a maltodextrin solution, glycerol, ethanol, etc. These materials may be used alone or in any combination of two or more thereof.

The composition including the pharmaceutically acceptable carrier may be in a variety of oral or parenteral formulations. The formulation may be prepared using diluents or excipients such as fillers, bulking agents, binders, wetting agents, disintegrants, etc., which are commonly used. Specifically, solid formulations for oral administration may include tablets, pills, powders, granules, capsules, etc. The solid formulations may be prepared by mixing the above compound with at least one excipient, for example, starch, calcium carbonate, sucrose, lactose, gelatin, etc. In addition to the simple excipients, lubricants such as magnesium stearate and talc may also be used. Liquid formulations for oral administration may include suspensions, solutions for internal use, emulsions, syrups, etc. In addition to simple diluents commonly used, such as water and liquid paraffin, many different excipients may also be used, for example, wetting agents, flavors, fragrances, preservatives, etc. Formulations for parenteral administration may include sterile aqueous solutions, non-aqueous solvents, suspensions, emulsions, lyophilized preparations, or suppositories. The non-aqueous solvents and the suspensions may include propylene glycol, polyethylene glycol, vegetable oil such as olive oil, injectable ester such as ethyloleate, etc. A base for the suppositories may include witepsol, macrogol, tween 61, cacao butter, laurin butter, glycerogelatin, etc.

The composition of the present invention may further include an antioxidant and a surfactant as an example of the pharmaceutically acceptable carrier. Specifically, the composition of the present invention may further include the antioxidant or may further include the surfactant, and more specifically, both antioxidant and surfactant.

In the composition of the present invention, the antioxidant refers to a material that is added for the purpose of terminating chain reactions of oxidation by acting on free radicals or peroxide generated during oxidation of active ingredients by oxygen in the air, and preventing progress of oxidation and deterioration of active ingredients.

In the present invention, since the antioxidant may prevent deterioration of the wound healing effect of the composition including SP, it may be used as an active ingredient of the wound healing composition.

Conventional antioxidants which may be used in the art may be used as the antioxidant without limitation, and specifically, any compound commercially available may be purchased or may be prepared by a conventional method known in the art, and any extract obtained from natural products or components contained therein may be used, but the antioxidants are not limited thereto, and any component which has the role of an antioxidant may be freely selected and used regardless of its route of entry. Specifically, β-mercaptoethanol (β-ME), glutathione (GSH), ascorbic acid, vitamin E, beta carotene, lycopene, coenzyme Q-10, selenium, chromium, magnesium, taurine, hypotaurine, trehalose, etc. may be used, but it is not limited thereto. Specifically, in the present invention, the antioxidant may be sodium thiosulfate.

A content of the antioxidant is not particularly limited, as long as it is able to prevent deterioration of the wound healing effect of the composition, but the content may be 0.01% by weight to 1% by weight with respect to the total weight of the composition of the present invention. Specifically, the content of the antioxidant may be 0.075% by weight to 1% by weight with respect to the total weight of the composition of the present invention.

In the composition of the present invention, the surfactant refers to a material that helps maintain a uniform liquid composition using hydrophobic oil components.

The surfactant may be a general surfactant commonly used in the preparation of pharmaceutical compositions, such as pharmaceutically acceptable anionic, cationic, nonionic, or amphiphilic surfactants, and specifically, any compound commercially available may be purchased or may be prepared by a conventional method known in the art, and any extract obtained from natural products or components contained therein may be used, but the surfactants are not limited thereto, and any component which has the role of an surfactant may be freely selected and used regardless of its route of entry. Specifically, in the present invention, the surfactant may be polysorbate 80.

A content of the surfactant may be 0.001% by weight to 0.1% by weight with respect to the total weight of the composition of the present invention. If the content of the surfactant is 0.001% by weight or less with respect to the total weight of the composition, emulsifying capacity of the composition of the present invention may be reduced to lower precipitation stability of the formulation. If the content is 0.1% by weight or more, there is a problem in that viscosity of the composition of the present invention may excessively increase, or phase inversion may occur. Specifically, the content of the surfactant may be 0.005% by weight to 0.1% by weight with respect to the total weight of the composition.

The term "wound healing", as used herein, means treatment or alleviation of a wound caused by an injury of skin cells, and the term "wound treatment" means all of the actions taken to alleviate or to be advantageous for the symptoms of the wound by administering the pharmaceutical composition of the present invention to a wounded subject.

The "subject" refers to all animals including humans, which have been already wounded or have possibility of being wounded. The animal may be mammals including not only humans but also cattle, horses, sheep, pigs, goats, camels, antelopes, dogs, cats, etc. in need of treating symptoms similar thereto, but is not limited thereto.

A specific example of the composition of the present invention may be a composition including SP, sodium thiosulfate, polysorbate 80, and sodium carboxymethylcellulose. Another specific example of the composition of the present invention may be a composition including SP, sodium thiosulfate, polysorbate 80, and hydroxyethyl cellulose.

The composition of the present invention may be a composition characterized by improving angiogenesis, epidermal regeneration, granulation tissue maturation, and collagen synthesis.

Specifically, in an Example of the present invention, it was demonstrated that the composition including the antioxidant, the surfactant, the thickener, and SP has excellent angiogenic effect (FIG. 5) and excellent epidermal regeneration effect (FIGS. 7A and 7B), compared to commercially available wound healing agents. Particularly, it was demonstrated that the pharmaceutical composition including hydroxyethyl cellulose as the thickener is excellent in the above effects, compared to pharmaceutical compositions including different kinds of thickeners.

Further, in an Example of the present invention, it was demonstrated that the composition including the antioxidant, the surfactant, the thickener, and SP forms mature granulation tissues (FIG. 8), and has excellent collagen-increasing effect (FIG. 9), compared to commercially available wound healing agents. Particularly, it was demonstrated that a composition including hydroxyethyl cellulose as the thickener is excellent in the above effects, compared to compositions including different kinds of thickeners.

The term "administering", as used herein, means introducing the pharmaceutical composition for wound healing of the present invention into a patient by any appropriate method. An administration route of the composition may be any route, as long as it allows the composition to reach a target tissue. The composition may be administered intraperitoneally, intravenously, intramuscularly, subcutaneously, intradermally, orally, topically, or intranasally, but is not limited thereto. The composition of the present invention may be administered by applying it on the skin, because of its feature of the wound healing effect.

The composition including the thickener, the antioxidant, the surfactant, and SP of SEQ ID NO: 1 may be administered in, a pharmaceutically effective amount.

The term "pharmaceutically effective amount" refers to an amount sufficient to treat diseases, at a reasonable benefit/risk ratio applicable to any medical treatment. An effective dose level may be determined in accordance with the type of a subject and severity, age and sex, activity of drug, sensitivity to drug, administration time, administration route, and excretion rate, duration of treatment, drugs used concurrently, and other factors known in the medical field. For example, the pharmaceutical composition may be administered in a daily dose of 0.0001 mg/kg to 1000 mg/kg, specifically, 0.001 mg/kg to 100 mg/kg.

The composition of the present invention may be administered either daily or intermittently, and the administration frequency may be once or 2 to 3 times a day. If each of two active ingredients is a single formulation, their administration frequency may be the same as or different from each other. Further, the composition of the present invention may be used alone or in combination with other drugs for wound healing. Considering all the above factors, it is important to administer a mininum amount that may achieve a maximum effect without side effects, which may be readily determined by those skilled in the art.

Another aspect of the present invention provides a quasi-drug composition for wound healing, including the thickener, the antioxidant, the surfactant, and SP of SEQ ID NO: 1.

The terms "thickener", "substance P (SP)", "antioxidant", "surfactant", and "wound healing", as used herein, are the same as described above.

The term "quasi-drug", as used herein, refers to fibers, rubber products, or similar products used for the purpose of treating, alleviating, curing, or preventing diseases in humans or animals. Additionally, as one of the formulations used for sterilization, insecticide, or a similar purpose in order to prevent an infection, non-appliance, non-machinery, or non-device used for the purpose of diagnosing, treating, alleviating, curing, or preventing diseases in humans or animals and for the purpose of exerting pharmacological effects upon the structure or functions of humans or animals. The quasi-drugs may also include personal hygiene products. The personal hygiene products may include disinfectant cleansers, shower foams, mouthwash, wet tissues, detergent soaps, hand wash, or ointments, but are not limited thereto. Specifically, with regard to the composition of the present invention, the quasi-drug may be a formulation for external application.

When used as a quasi-drug additive, the composition of the present invention may be added as it is, or used in combination with another quasi-drug or quasi-drug component according to a conventional method. Amounts of the active ingredient in the mixture may be properly determined depending on the purpose of use.

MODE FOR INVENTION

Hereinafter, the constitutions and effects of the present invention will be described in more detail with reference to the Examples. However, these Examples are for illustrative purposes only, and the invention is not intended to be limited by these Examples.

Example 1

Cell Proliferative Effect of SP Treatment on Human Dermal Fibroblast Cells

The cell proliferative effect of SP was analyzed by MTT assay.

In detail, 100 μl of a human dermal fibroblast cell suspension of $3 \times 10^4$ CFU/ml was put in a 96-well culture plate, and incubated for 24 hours. FGM medium (fibroblast growth medium; fibroblast basal medium containing hFGF-B, insulin, fetal bovine serum (FBS), gentamicin, and amphotericin-B) were removed, and then 180 μl of fresh FGM medium was dispensed into each well, and then 20 μl of SP diluted with phosphate buffered saline (PBS) was inoculated by varying its concentration (0.1, 1, 5, 10, 50, and 100 μg/ml).

Meanwhile, 20 μl of phosphate buffered saline was used as a negative control group. After inoculation, cells were incubated at 37° C. for 48 hours, and then the medium, SP, and negative control group were removed. The cells were washed with the phosphate buffered saline three times. 90 μl of FGM medium was mixed with 10 μl of MTT solution (0.5 mg/ml), and treated to each well, and allowed to react at 37° C. for 4 hours.

Finally, the cells were washed with the phosphate buffered saline, and stirred in 150 μl of isopropyl alcohol solution for 10 minutes, and absorbance at 570 nm was measured.

As a result, SP was found to increase cell proliferation of human dermal fibroblast cells in all concentration groups of 0.1 μg/ml to 100 μg/ml. Specifically, the cell proliferation rates in all concentration groups were found to be 170% or more. Particularly, when the concentration of SP was 5 μg/ml, the cell proliferation rate was 200% or more, indicating that it shows an excellent cell proliferative effect, compared to other concentration groups, and SP of 5 μg/ml also showed about 2.2 times or higher proliferation rate, compared to the negative control group (FIG. 1).

Accordingly, it was confirmed that SP shows an excellent cell proliferative effect without cytotoxicity and therefore, it may be used as a pharmaceutical composition for wound healing.

Example 2

Test of Stability of SP According to Contents of Antioxidant and Surfactant

A novel composition was prepared by using an antioxidant and a surfactant, in addition to SP which was confirmed to show the cell proliferative effect on human dermal fibroblast cells in Example 1. In this regard, optimal contents of the antioxidant and the surfactant in the composition were confirmed by testing stability of SP according to contents of the antioxidant and the surfactant.

To SP, sodium thiosulfate was added as the antioxidant by varying its content (0.05% by weight, 0.1% by weight, 0.5% by weight and 1% by weight), and polysorbate 80 was added as the surfactant by varying its content (0.003% by weight, 0.006% by weight, 0.01% by weight, 0.05% by weight and 0.1% by weight) to prepare compositions. Stability of SP in respective formulations having the above different contents of sodium thiosulfate and polysorbate 80 was analyzed by using SP ELISA kit.

Figure 2:
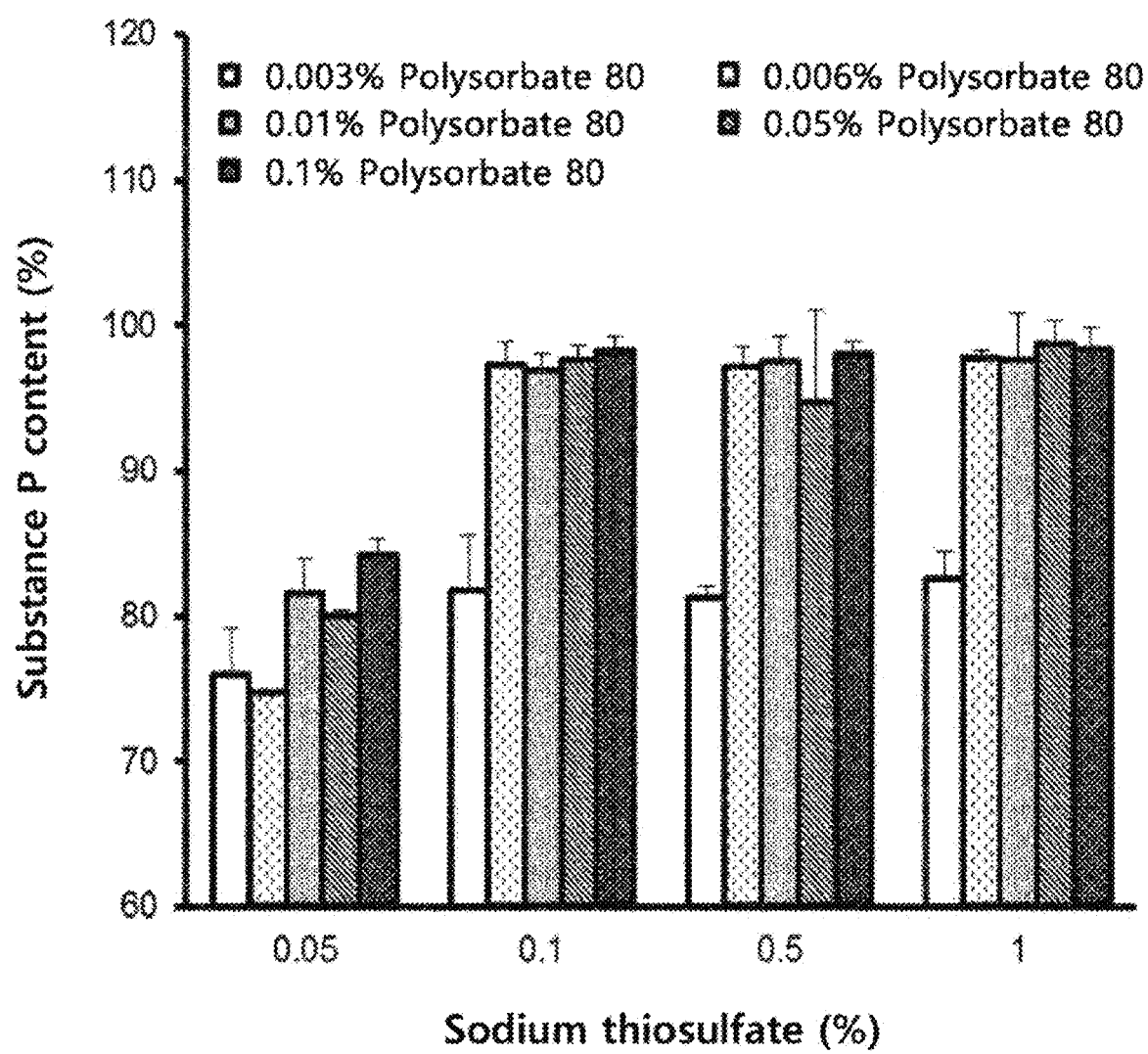
FIG. 2 is a graph showing stability of SP according to contents of an antioxidant and a surfactant.

As shown in FIG. 2, it was confirmed that in the composition including 0.1% by weight or more of sodium thiosulfate, stability of SP generally increased. It was also confirmed that in the composition including 0.006% by weight or more of polysorbate 80, stability of SP increased, and the effect according to the content of polysorbate 80 was more obvious when the content of sodium thiosulfate was 0.1% by weight or more.

Example 3

Preparation of Novel Formulations for Wound Healing Including SP

The present inventors prepared novel formulations using an antioxidant, a surfactant and a thickener, in addition to SP. SP was synthesized through solid/solution phase using Fmoc-chemistry which is a peptide synthesis technology, and purified by high performance liquid chromatography. Finally, SP with purity of 85% or more was used. Of the novel formulations, a formulation including carboxymethyl cellulose as the thickener was prepared as in the ingredients and contents of the following Table 1.

TABLE 1

Formulation including SP and carboxymethyl cellulose (SP + CMC + polysorbate 80 + sodium thiosulfate formulation)

| Composition of formulation | Content |
|---|---|
| Sodium carboxymethylcellulose | 1.5% |
| Polysorbate 80 | 0.006% |
| Sodium thiosulfate | 0.1% |
| SP | 5 μg/ml |

Further, of the novel formulations, a formulation including hydroxyethyl cellulose as the thickener was prepared as in the ingredients and contents of the following Table 2.

TABLE 2

Formulation including SP and hydroxyethyl cellulose (SP + HEC + polysorbate 80 + sodium thiosulfate formulation)

| Composition of foimulation | Content |
|---|---|
| Hydroxyethyl cellulose | 1.5% |
| Polysorbate 80 | 0.006% |
| Sodium thiosulfate | 0.1% |
| SP | 5 μg/ml |

Example 4

Wound Healing Effect of Novel Formulations in Skin Wound Mouse Model

Example 4-1

Preparation of Skin Wound Mouse Model and Administration of Novel Formulation

To compare wound healing effects between novel formulations including SP (SP+CMC+polysorbate 80+sodium thiosulfate formulation and SP+HEC+polysorbate 80+sodium thiosulfate formulation), full-thickness skin wound models were prepared. Commercially available wound healing agents, Madecassol care ointment (Dongguk Pharmaceuticals, Korea) and Easyef cell regenerating ointment (Daewoong Pharmaceuticals) were used as positive control groups.

In detail, 7-week-old BALB/c female mice (DooYeol Biotech) were acclimated for 1 week, and then anesthetized by an intraperitoneal injection of a mixture of Ketamine and rumpun. The dorsal hair was removed using an electric razor and a hair removal cream (Veet). Povidone and 70% ethanol were used to disinfect the area from which the epidermis was to be removed, and a 5-mm biopsy punch was used to apply a full-thickness wound on both sides of the lower buttocks, while avoiding the spine of the mouse. To prevent spontaneous wound contraction by the superficial muscle of the mouse, a silicone ring with an outer diameter of 15 mm and an inner diameter of 8 mm was attached around the wounded area using suture threads.

Thereafter, to the wound site, phosphate buffered saline as the negative control was administered, and Madecassol care and Easyef cell regenerating ointments as the positive controls were administered. As experimental groups, 5 μg/ml of SP, SP+CMC+polysorbate 80+sodium thiosulfate formulation and SP+HEC+polysorbate 80+sodium thiosulfate formulation which are the novel formulations were administered. Specifically, each 30 μl of SP and each novel formulations were administered to the full-thickness wound once a day for 5 days.

Example 4-2

Wound Size-Reducing Effect of Novel Formulation in Skin Wound Mouse Model

As in Example 4-1, the novel formulations were administered to the skin wound mouse models, and then reduction in the wound size was evaluated to compare the wound size-reducing effects. In detail, the reduced wound size was calculated as the size of wound area by analyzing an image of the wound at 0 day and 6 days after administration of the novel formulations. The size of wound area was quantified by using Photoshop.

The size of the wound was examined with the naked eye, and as a result, it was confirmed that the novel formulations have an excellent wound size-reducing effect, compared to SP. Specifically, it was confirmed with the naked eye that 6 days after administration with the novel formulations (SP+CMC+polysorbate 80+sodium thiosulfate, and SP+HEC+polysorbate 80+sodium thiosulfate), the size of the wound was reduced, compared to treatment with SP (FIG. 3A).

The size of the wound area was also quantified, and as a result, it was found that all novel formulations have superior wound size-reducing effects. Specifically, the wound area was about 40% or more upon administration of SP, whereas the wound area was about 20% upon treatment of the novel formulations, indicating that the wound size-reducing effect of the novel formulations is at least twice higher.

In particular, the result of quantifying the wound size showed that when the formulation using hydroxyethyl cellulose as the thickener (SP+HEC+polysorbate 80+sodium thiosulfate) of the novel formulations was administered, the wound size was 20% or less (FIG. 3B), indicating that the novel formulations including SP (SP+CMC+polysorbate 80+sodium thiosulfate and SP+HEC+polysorbate 80+sodium thiosulfate) have an excellent wound size-reducing effect, compared to SP alone.

Furthermore, the wound size-reducing effects of the novel formulations and the positive control were quantified, and as a result, of the novel formulations, SP+CMC+polysorbate 80+sodium thiosulfate has an excellent wound size-reducing effect, compared to Madecassol ointment, and its effect was similar to that of Easyef ointment. In contrast, it was confirmed that SP+HEC+polysorbate 80+sodium thiosulfate has an excellent reducing effect, compared to all positive control groups (FIG. 3C).

These results suggest that the novel formulations have excellent wound size-reducing effects, compared to commercially available wound healing agents. Specifically, it was confirmed that of the novel formulations, SP+HEC+polysorbate 80+sodium thiosulfate formulation has better effect than SP+CMC+polysorbate 80+sodium thiosulfate formulation.

Further, under the same experimental conditions, the wound healing effect was compared between single administration of SP and administration of SP+Only HEC. At 0 day and 6 days, the size of each wound was examined with the naked eye, and as a result, it was confirmed with the naked eye that there was no significant difference in the wound size between administration of SP and administration of SP+Only HEC (FIG. 4A). The size of the wound area was quantified, and as a result, in both cases of administration of SP and administration of SP+Only HEC, the wound size was about 40% or more (FIG. 4B).

These results show that SP and SP+Only HEC have similar wound healing effects. As described above, the wound healing effect of the novel SP+HEC+polysorbate 80+sodium thiosulfate formulation is at least twice higher, compared to that of SP (FIGS. 3A and 3B), suggesting that the novel SP+HEC+polysorbate 80+sodium thiosulfate formulation has a twice or higher wound healing effect, compared to SP+Only HEC.

Example 4-3

Angiogenic Effect of Novel Formulation in Skin Wound Mouse Model

As in Example 4-1, the novel formulations were administered to the skin wound mouse models, and then angiogenic effects were compared. In detail, increased angiogenesis was confirmed by examining an image of angiogenesis on the skin tissue with the naked eye after biopsy of the skin tissue of the wound area 6 days after administration of the novel formulations.

As a result, it was confirmed that the novel formulations have excellent angiogenic effects, compared to SP. Specifically, there was a slight difference in the wound size between the SP-administered group and non-treatment group, and angiogenesis was also insignificant. In contrast, reduction of the wound size and formation of many new blood vessels around the wound area were observed in the novel formulation-administered groups. Particularly, it was confirmed that SP+CMC+polysorbate 80+sodium thiosulfate formulation and SP+HEC+polysorbate 80+sodium thiosulfate formulation have excellent wound size-reducing and angiogenic effects, compared to Madecassol care and Easyef cell regenerating ointments which are commercially available wound healing agents (FIG. 5)

Example 4-4

Dermal Regeneration Effect of Novel Formulation in Skin Wound Mouse Model

As in Example 4-1, the novel formulations were administered to the skin wound mouse models, and then reduced dermal gaps (DG) were measured to examine dermal regeneration effects. In detail, biopsies of the skin tissues of the wound areas were taken 6 days after administration of the novel formulations, and then fixed in 10% formalin, followed by hematoxylin & eosin (H&E) staining. After staining, the dermal gaps were measured to examine dermal regeneration in the wounded tissues.

A graph for quantifying the dermal gaps and tissue images were analyzed, and as a result, similar dermal regeneration was observed in all administration groups including the SP-administered group. Particularly, of the novel formulations, SP+HEC+polysorbate 80+sodium thiosulfate formulation showed the most excellent dermal regeneration (FIGS. 6A and 6B).

Example 4-5

Epidermal Regeneration Effect of Novel Formulation in Skin Wound Mouse Model

As in Example 4-1, the novel formulations were administered to the skin wound mouse models, and then reduced epidermal gaps (EG) were measured to examine epidermal regeneration effects. In detail, biopsies of the skin tissues of the wound areas were taken 6 days after administration of the novel formulations, and then, the skin tissues were fixed in 10% formalin, followed by hematoxylin & eosin (H&E) staining. After staining, the epidermal gaps were measured to examine epidermal regeneration in the wounded tissues.

A graph for quantifying epidermal gaps and tissue images were analyzed, and as a result, it was confirmed that the epidermal gaps were reduced in all administration groups including SP-administered group, compared to the control groups. Specifically, the epidermal gaps were reduced to about 60% upon administration of SP, and the epidermal gaps were reduced to 60% or less upon administration of Madecassol care and Easyef cell regenerating ointments which are commercially available wound healing agents. In contrast, the epidermal gap was reduced to 30% or less upon administration of the novel formulation, indicating that the epidermal regeneration effect of the novel formulation is at least twice higher than that of the commercially available products. Furthermore, it was confirmed that SP+HEC+polysorbate 80+sodium thiosulfate formulation has excellent epidermal regeneration effect, compared to SP+CMC+polysorbate 80+sodium thiosulfate formulation (FIGS. 7A and 7B).

Example 4-6

Granulation Tissue Maturation Effect of Novel Formulation in Skin Wound Mouse Model As in Example 4-1, the novel formulations were administered to the skin wound mouse models, and then granulation tissue maturation on the wound tissue was examined. In detail, biopsies of the skin tissues of the wound areas were taken 6 days after administration of the novel formulations, and then the skin tissues were fixed in 10% formalin, followed by hematoxylin & eosin (H&E) staining. After staining, granulation tissue maturation was examined.

As a result, Madecassol care ointment-administered group and Easyef cell regenerating ointment-administered, group which are positive control groups, and SP and novel formulations, which are experimental groups, showed compact granulation tissue formation, compared to the negative control group. Particularly, in case of the SP+HEC+polysorbate 80+sodium thiosulfate formulation, fibroblasts constituting dermal tissues were observed to be mature in a stable and flat shape, indicating that SP+HEC+polysorbate 80+sodium thiosulfate formulation is able to form the most mature granulation tissue (FIG. 8).

Example 4-7

Collagen-Increasing Effect of Novel Formulation in Skin Wound Mouse Model

As in Example 4-1, the novel formulations were administered to the skin wound mouse models, and then the degree of increase of collagen of wound tissues was examined. In detail, biopsies of the skin tissues in the wound areas were taken 6 days after administration of the novel formulations, and then the skin tissues were fixed in 10% formalin, followed by Massons Trichrome staining. After staining, the degree of increase of collagen in the wound tissue was examined.

As a result, when the novel formulation was administered, stronger staining was exhibited compared to SP, indicating that the novel formulations have an excellent collagen-increasing effect. In particular, SP+CMC+polysorbate 80+sodium thiosulfate formulation and SP+HEC+polysorbate 80+sodium thiosulfate formulation showed stronger staining than Madecassol care and Easyef cell regenerating ointments which are commercially available wound healing agents, indicating that the formulations have an excellent collagen-increasing effect. Furthermore, the SP+HEC+polysorbate 80+sodium thiosulfate formulation has an excellent collagen-increasing effect, compared to SP+CMC formulation (FIG. 9).

Therefore, the novel formulations including SP of the present invention have an excellent wound healing effect, compared to SP alone and Madecassol care and Easyef cell regenerating ointments which are commercially available products. Particularly, it was confirmed that of the novel formulations, the formulation including SP and hydroxyethyl cellulose has the most excellent wound healing effect.

Example 5

Test of Stability of SP+HEC+Polysorbate 80+Sodium Thiosulfate Formulation by Varying Medium and Temperature Stability of SP in the SP+HEC+polysorbate 80+sodium thiosulfate formulation used in Example 4-1 was examined over time. SP and SP of SP+HEC+polysorbate 80+sodium thiosulfate formulation were stored in cell growth media for human epithelial keratinocyte (HEK) culture (keratinocyte growth media; KGM) and human dermal fibroblast (HDF) culture (fibroblast growth media; FGM).

Each sample was taken out of the media after a predetermined period of time (0 hr, 3 hrs, 6 hrs, 12 hrs and 24 hrs), and diluted with phosphate buffered saline, and then the SP content in each sample was analyzed using SP ELISA kit.

Further, it was examined with respect to whether SP stability in each sample was maintained at different temperatures. SP and SP of SP+HEC+polysorbate 80+sodium thiosulfate formulation were stored at 60° C., 37° C., RT, and 4° C. for 4 weeks, respectively. The samples before storage were used as control groups. SP stability was analyzed using SP ELISA kit.

The results of examining SP stability showed that the novel SP+HEC+polysorbate 80+sodium thiosulfate formulation maintained high SP stability without changes in the SP content in both KGM and FGM media, whereas the single formulation of SP showed reduction in the SP content over time, confirming reduced SP stability (FIGS. 10A and 10B).

Further, under all temperature conditions, the single formulation of SP showed a lower SP content than the SP+HEC+polysorbate 80+sodium thiosulfate formulation, and showed changes in the SP content according to temperature changes. In contrast, the SP+HEC+polysorbate 80+sodium thiosulfate formulation maintained a high SP content under all temperature conditions, and was not greatly influenced by temperature changes (FIG. 10C).

These results showed that the SP+HEC+polysorbate 80+sodium thiosulfate formulation has higher SP stability than the single formulation of SP, indicating that stability of SP is improved by adding HEC, polysorbate 80, and sodium thiosulfate to SP.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

What is claimed is:

1. A method of treating a wound, comprising administering a composition comprising a thickener, an antioxidant, a surfactant, and substance P consisting of an amino acid sequence of SEQ ID NO: 1 to a subject in need thereof,
    wherein the thickener is hydroxyethyl cellulose;
    wherein the antioxidant is sodium thiosulfate; and
    wherein the surfactant is polysorbate 80.

2. The method of claim 1, wherein a concentration of the substance P is 0.1 µg/ml to 100 µg/ml.

3. The method of claim 1, wherein a concentration of the substance P is 3 µg/ml to 8 µg/ml.

4. The method of claim 1, wherein a content of the thickener is 1% by weight to 20% by weight with respect to the total weight of the composition.

5. The method of claim 1, wherein a content of the antioxidant is 0.01% by weight to 1% by weight with respect to the total weight of the composition.

6. The method of claim 1, wherein a content of the surfactant is 0.001% by weight to 0.1% by weight with respect to the total weight of the composition.

7. The method of claim 1, wherein a content of the antioxidant is 0.075% by weight to 1% by weight with respect to the total weight of the composition.

8. The method of claim 1, wherein a content of the surfactant is 0.005% by weight to 0.1% by weight with respect to the total weight of the composition.

* * * * *